(12) United States Patent
Miller et al.

(10) Patent No.: US 6,471,707 B1
(45) Date of Patent: Oct. 29, 2002

(54) BONE SCREW HAVING BIORESORBABLE PROXIMAL SHAFT PORTION

(75) Inventors: Stuart D. Miller, Owings Mills, MD (US); James S. Babcock; Tim Lessek, both of Warsaw, IN (US); Mark Vanderwalle, Pierceton, IN (US)

(73) Assignee: Biomet, Warsaw, IN (US)

( * ) Notice: Subject to any disclaimer, the term of this patent is extended or adjusted under 35 U.S.C. 154(b) by 0 days.

(21) Appl. No.: 09/853,425

(22) Filed: May 11, 2001

(51) Int. Cl.[7] .............................................. A61B 17/58
(52) U.S. Cl. ............................... 606/73; 606/72; 606/77
(58) Field of Search ............................... 606/72, 73, 74, 606/75, 76, 77, 78, 79, 80, 104, 105, 219, 220; 623/16.11, 17.11, 20.11; 411/81, 166

(56) References Cited

U.S. PATENT DOCUMENTS

| | | |
|---|---|---|
| 4,776,329 A | 10/1988 | Treharne |
| 4,973,333 A | 11/1990 | Treharne |
| 5,169,400 A | 12/1992 | Muhling et al. |
| 5,470,334 A | 11/1995 | Ross et al. |
| 5,522,817 A * | 6/1996 | Sander et al. |
| 5,695,497 A | 12/1997 | Stahelin |
| 5,827,285 A * | 10/1998 | Bramlet |
| 6,048,344 A | 4/2000 | Schenk |
| 6,096,060 A | 8/2000 | Fitts et al. |
| 6,241,732 B1 * | 6/2001 | Overaker et al. |
| 6,290,701 B1 * | 9/2001 | Enayati |

FOREIGN PATENT DOCUMENTS

| | | |
|---|---|---|
| DE | WO 89/09030 | 10/1989 |
| DE | WO 91/06252 | 5/1991 |

* cited by examiner

Primary Examiner—Pedro Philogene
(74) Attorney, Agent, or Firm—Harness, Dickey & Pierce, P.L.C.

(57) ABSTRACT

A fixation device, such as a bone screw, includes a bioresorbable proximal shaft portion and a non-bioresorbable distal threaded portion. In one aspect, the shaft portion is provided with a longitudinal throughbore which is aligned with a corresponding longitudinal bore in the proximal region of the threaded portion. A driver mechanism is employed to impart a rotary force so as to enable the device to be inserted into bone tissue. Afterwards, the driver mechanism is withdrawn from the respective bores. In another aspect, the non-bioresorbable distal portion is a substantially elongated solid member and includes a threaded distal region and a shaft-like proximal region. The comparatively smaller bioresorbable proximal region can mate with the distal portion either after or before the distal portion has been inserted into the bone tissue.

64 Claims, 11 Drawing Sheets

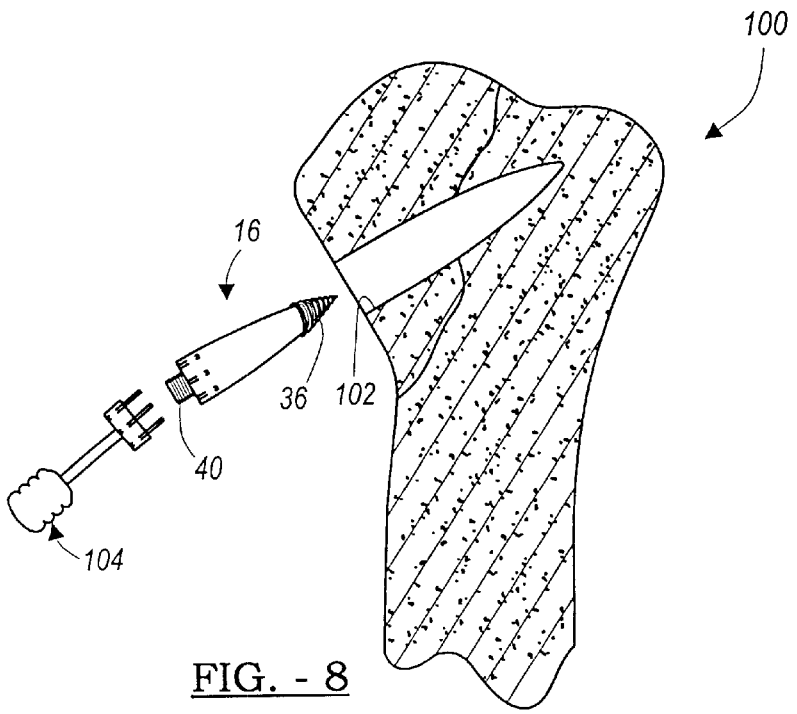
FIG. - 8
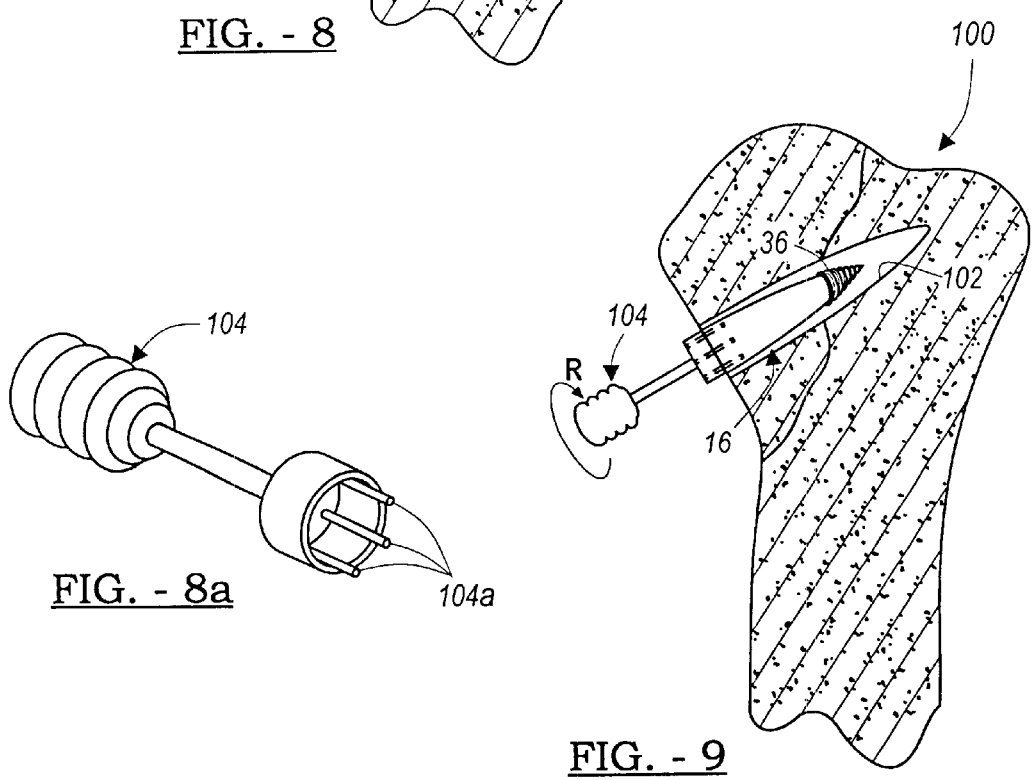
FIG. - 8a
FIG. - 9

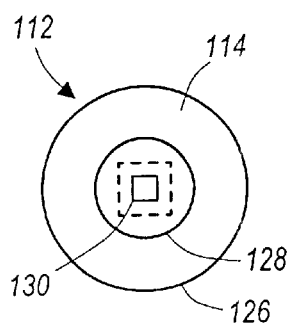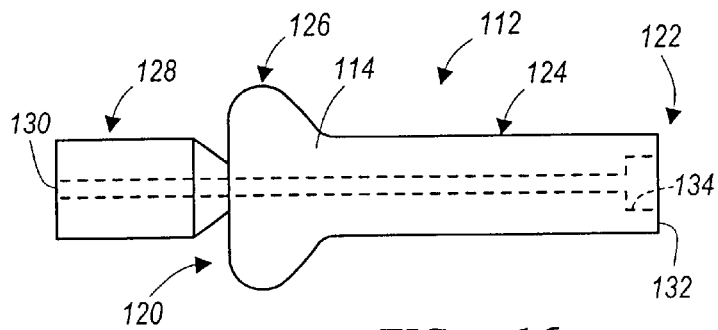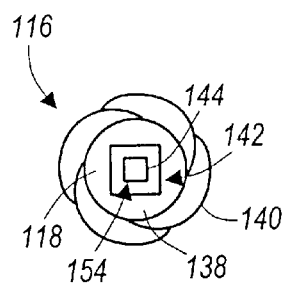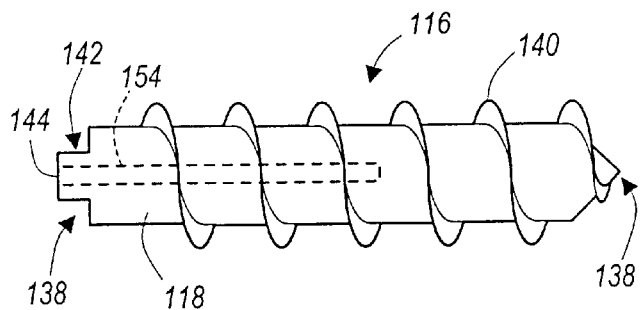
FIG. - 15
FIG. - 16
FIG. - 17
FIG. - 18
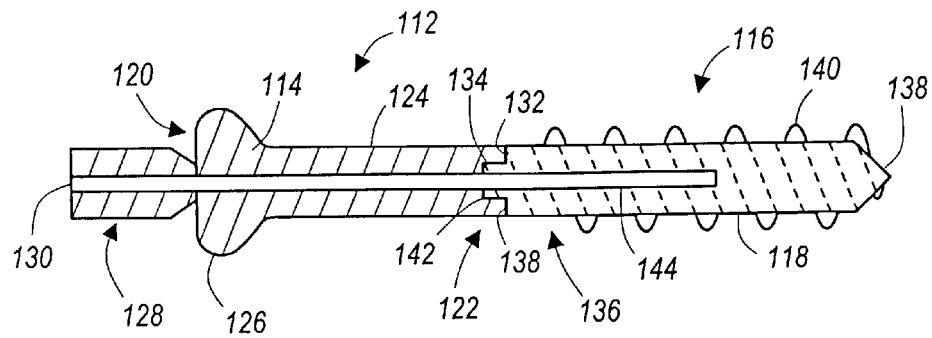
FIG. - 19

BONE SCREW HAVING BIORESORBABLE PROXIMAL SHAFT PORTION

BACKGROUND

The present invention relates generally to bioresorbable devices, and more particularly, to new and improved bone screws having bioresorbable shaft portions and non-resorbable threaded portions, wherein specially adapted driver mechanisms are capable of delivering a torque force about the non-resorbable threaded portion during insertion of the bone screw into bone tissue, thus eliminating, or at least lessening, the torque stresses at the bioresorbable shaft portion/non-resorbable threaded portion junction. Additionally, different sizes of bioresorbable shaft portions, non-resorbable threaded portions, and driver mechanisms may be incorporated into a kit system.

Bone screws are generally defined as a threaded device which is inserted into bone tissue. The intended function of bone screws is to immobilize bones or bone fragments or to affix other orthopedic devices, such as metal bone plates or bone rods, to, or within, bones. Although bone screws are typically comprised of metallic materials (e.g., stainless steel, titanium, cobalt-chrome alloys, and the like), they may also be comprised of other materials, such as bioresorbable materials (e.g., hydroxyapatite, poly-lactic acid, poly-glycolic acid, and the like). The terms "bioresorbable," "biodegradable," "absorbable," and "bioabsorbable" are used interchangeably herein.

The use of bioresorbable bone screws in connection with the treatment of various bone defects, such as fractures, and the like, is fairly well known in the art. These bioresorbable bone screws have enabled the medical community to achieve excellent surgical results, even under difficult clinical conditions.

The main benefit of using bioresorbable devices is that the devices resorb into the body over a generally predictable time period once a sufficient level of healing has occurred, for example, at the junction of a bone fracture, thus negating the need for subsequent removal of the device. By having the device resorb, the likelihood of osteolysis, stress fractures, and inflammatory immune system responses are greatly reduced. For example, a protruding head portion of a metallic bone screw may occasionally cause irritation of the surrounding skeletal tissues at the insertion site.

One resorbable material of particular interest is marketed by Biomet, Inc. (Warsaw, Indiana) under the tradename LACTOSORB®. LACTOSORB® is an absorbable co-polymer synthesized from all-natural ingredients: 82% L-lactic acid and 18% glycolic acid, unlike the homopolymers in common use such as 100% poly-L-lactic acid (PLLA) or 100% poly-glycolic acid (PGA), LACTOSORB® copolymer is substantially amorphous (i.e., without crystallinity), meaning that its degradation is uniform, precluding the crystalline release associated with degrading copolymers that have been associated with late inflammatory reactions. Furthermore, the LACTOSORB® copolymer ratio permits the polymer to retain most of it's strength for six to eight weeks, which is appropriate for healing, but not so long as to raise concerns about long-term stress shielding of bone.

Examples of surgical devices comprised of bioresorbable materials can be found with reference to the following U.S. Patents:

U.S. Pat. No. 5,695,497 to Stahelin discloses a screw made of biodegradable material for bone surgery purposes, wherein the outer surface of the screw body is provided with a coaxial external thread. A coaxial channel of saw-toothed star-shaped transverse cross-sectional profile is provided in the screw body, which channel is open at the proximal end in order to receive the complementary shaft of a screwdriver, and extends into the area of the distal end.

U.S. Pat. No. 6,096,060 to Fitts et al. disclose a bioabsorbable soft tissue anchor system comprising a cannulated soft tissue anchor for being turned through soft tissue, and a driver for driving the anchor and method for attaching soft tissue at a selected site of implantation. The soft tissue anchor is an elongated unitary body having a threaded distal section, a non-threaded proximal section, a transverse proximal head and a non-circular axial throughbore. The anchor is used with a driver having a driving shaft with a pointed tip and a cross-section adapted to engage the anchor's axial throughbore. The driving shaft is longer than the anchor so that the anchor may be placed on the shaft leaving the tip exposed to permit tissue to be pierced and placed adjacent a pre-formed hole at the site of implantation. Simultaneous pushing and turning of the driver will advance the anchor through the tissue and into the pre-formed hole.

Recently, there has been increased interest in employing bone screws, and other surgical devices, that are comprised of both metallic and bioresorbable portions, in order to take advantage of the respective merits of each type of material.

U.S. Pat. No. 5,522,817 to Sander et al. disclose a self-inserting absorbable orthopedic fixation device having a bioabsorbable fastening body portion for fastening body tissue, and having bone penetrating elements such as hard, pointed tips for penetrating bone or hard tissue fixed thereto. The pointed tips may be fabricated from metals or ceramics. The fixation device may be in the form of staples, pins, screws, and the like. The two components may be provided with mating surfaces (e.g., threaded external surface and threaded internal surface, lip and groove, and the like) that allow the two components to be simultaneously driven into tissue.

The main disadvantage of the this type of fixation device is that application of a rotary force (e.g., during insertion into bone tissue) produces a significant amount of torque at the bioresorbable portion/non-bioresorbable portion junction or interface. This torque force can potentially lead to failure of the fixation device, especially at the bioresorbable portion/non-bioresorbable portion junction or interface. The surgeon would then be required to retrieve the various pieces of the fixation device from the patient's body, if possible, and attempt another fixation procedure.

Therefore, there exists a need for a fixation device, such as a bone screw, wherein the device can be provided with a proximal bioresorbable shaft portion and a distal non-bioresorbable threaded portion, wherein a driver mechanism is capable of delivering a torque force about the non-resorbable threaded portion during insertion of the bone screw into bone tissue, thus eliminating, or at least lessening, the torque stresses at the bioresorbable shaft portion/non-resorbable threaded portion junction. There also exists a need for a kit having different sizes of bioresorbable shaft portions, non-resorbable threaded portions, and driver mechanisms.

SUMMARY OF THE INVENTION

In accordance with a first embodiment of the present invention, an orthopedic fixation system is provided, comprising a first member comprised of a bioresorbable material, the first member having a distal and proximal region, and a second member comprised of a non-resorbable material, the second member having a distal and proximal region. The distal region of the first member is adapted to selectively mate with the proximal region of the second member. The second member is substantially elongated with respect to the first member. The distal region of the second member is provided with an external threaded surface thereon.

In accordance with a second embodiment of the present invention, an orthopedic fixation system kit is provided, comprising a receptacle. The receptacle contains a plurality of first members comprised of a bioresorbable material and each having a different size, each of the first members having a distal and proximal region and a plurality of second members comprised of a non-resorbable material and each having a different size, each of the second members having a distal and proximal region. The distal region of each first member is adapted to selectively mate with the proximal region of each second member that has a corresponding size. The second member is substantially elongated with respect to the first member. The distal region of the second member is provided with an external threaded surface thereon.

In accordance with a third embodiment of the present invention, a method of affixing an orthopedic device to bone tissue is provided, comprising providing a fixation device, including a first member comprised of a bioresorbable material, the first member having a distal and proximal region, and a second member comprised of a non-resorbable material, the second member having a distal and proximal region. The distal region of the first member is adapted to selectively mate with the proximal region of the second member. The second member is substantially elongated with respect to the first member. The distal region of the second member is provided with an external threaded surface thereon. Also provided is a driver member adapted to be engaged by either the first member or the second member. A rotary force is applied to the driver member so as to cause either the first member or the second member to be inserted into the bone tissue such that either the first member or the second member is brought into abutting engagement with the bone tissue.

In accordance with a fourth embodiment of the present invention, a method of joining two bone fragments is provided, comprising providing a fixation device, including a first member comprised of a bioresorbable material, the first member having a distal and proximal region, and a second member comprised of a non-resorbable material, the second member having a distal and proximal region. The distal region of the first member is adapted to selectively mate with the proximal region of the second member. The second member is substantially elongated with respect to the first member. The distal region of the second member is provided with an external threaded surface thereon. Also provided is a driver member adapted to engage either the first member or the second member. A rotary force is applied to the driver member so as to cause either the first member or the second member to be inserted into at least one of the bone fragments so as bring both of the bone fragments together into abutting engagement.

In accordance with a fifth embodiment of the present invention, an orthopedic fixation system is provided, comprising a first member comprised of a bioresorbable material, the first member having a distal and proximal region, and a second member comprised of a non-resorbable material, the second member having a distal and proximal region. The distal region of the first member is adapted to selectively mate with the proximal region of the second member. The first member is provided with a throughbore extending along a longitudinal axis thereof. The second member is provided with a bore extending from the proximal region towards the distal region thereof. The second member is provided with an external threaded surface thereon.

In accordance with a sixth embodiment of the present invention, an orthopedic fixation system is provided, comprising a first member comprised of a bioresorbable material, the first member having a distal and proximal region, and a second member comprised of a non-resorbable material, the second member having a distal and proximal region. The distal region of the first member is adapted to selectively mate with the proximal region of the second member. The first member is provided with a throughbore extending along a longitudinal axis thereof. The second member is provided with a bore extending from the proximal region towards the distal region thereof. The second member is provided with an external threaded surface thereon. A driver member is adapted to be received simultaneously within the throughbore of the first member and the bore of the second member.

In accordance with a seventh embodiment of the present invention, an orthopedic fixation system kit is provided, comprising a receptacle. The receptacle contains a plurality of first members comprised of a bioresorbable material and each having a different size, each of the first members having a distal and proximal region, and a plurality of second members comprised of a non-resorbable material and each having a different size, each of the second members having a distal and proximal region. The distal region of each first member is adapted to selectively mate with the proximal region of each second member that has a corresponding size. Each first member is provided with a throughbore extending along a longitudinal axis thereof. Each second member is provided with a bore extending from the proximal region towards the distal region thereof. Each second member is provided with an external threaded surface thereon. The kit also contains at least one driver member adapted to be received simultaneously within the throughbore of each first member and the bore of each second member.

In accordance with an eighth embodiment of the present invention, a method of affixing an orthopedic device to bone tissue is provided, comprising providing a fixation device. The fixation device includes a first member comprised of a bioresorbable material, the first member having a distal and proximal region, and a second member comprised of a non-resorbable material, the second member having a distal and proximal region. The distal region of the first member is adapted to selectively mate with the proximal region of the second member. The first member is provided with a throughbore extending along a longitudinal axis thereof. The second member is provided with a bore extending from the proximal region towards the distal region thereof. The second member is provided with an external threaded surface thereon. Also provided is a driver member adapted to be received simultaneously within the throughbore of the first member and the bore of the second member. A rotary force is applied to the driver member so as to cause the fixation device to be inserted into the bone tissue such that the orthopedic device is brought into abutting engagement with the bone tissue.

In accordance with a ninth embodiment of the present invention, a method of joining two bone fragments is provided, comprising providing a fixation device. The fixation device includes a first member comprised of a bioresorbable material, the first member having a distal and proximal region, and a second member comprised of a non-resorbable material, the second member having a distal and proximal region. The distal region of the first member is adapted to selectively mate with the proximal region of the second member. The first member is provided with a throughbore extending along a longitudinal axis thereof. The second member is provided with a bore extending from the proximal region towards the distal region thereof. The second member is provided with an external threaded surface thereon. Also provided is a driver member adapted to be received simultaneously within the throughbore of the first member and the bore of the second member. A rotary force is applied to the driver member so as to cause the fixation device to be inserted into both of bone fragments so as bring both of the bone fragments together into abutting engagement.

A more complete appreciation of the present invention and its scope can be obtained from the following detailed description of the invention and the appended claims.

BRIEF DESCRIPTION OF THE DRAWINGS

The present invention will become more fully understood from the detailed description and the accompanying drawings, wherein:

FIG. 8 illustrates a partial sectional view of a distal portion of an orthopedic fixation system about to be inserted into a fracture site of a femur head, in accordance with one embodiment of the present invention;

FIG. 8A illustrates a perspective view of a driver member, in accordance with one embodiment of the present invention;

FIG. 9 illustrates a partial sectional view of a distal portion of an orthopedic fixation system partially inserted into a fracture site of a femur head, in accordance with one embodiment of the present invention;

FIG. 15 illustrates a top plan view of the proximal portion of the orthopedic fixation system depicted in FIG. 14, in accordance with an alternative embodiment of the present invention;

FIG. 16 illustrates an elevational view of the proximal portion of the orthopedic fixation system depicted in FIG. 14, in accordance with an alternative embodiment of the present invention;

FIG. 17 illustrates a top plan view of the distal portion of the orthopedic fixation system depicted in FIG. 14, in accordance with an alternative embodiment of the present invention;

FIG. 18 illustrates an elevational view of the distal portion of the orthopedic fixation system depicted in FIG. 14, in accordance with an alternative embodiment of the present invention;

FIG. 19 illustrates an elevational view of the proximal and distal portions of the orthopedic fixation system depicted in FIG. 14 in abutting engagement, in accordance with an alternative embodiment of the present invention;

The same reference numerals refer to the same parts throughout the various Figures.

DETAILED DESCRIPTION OF THE INVENTION

Figure 1:
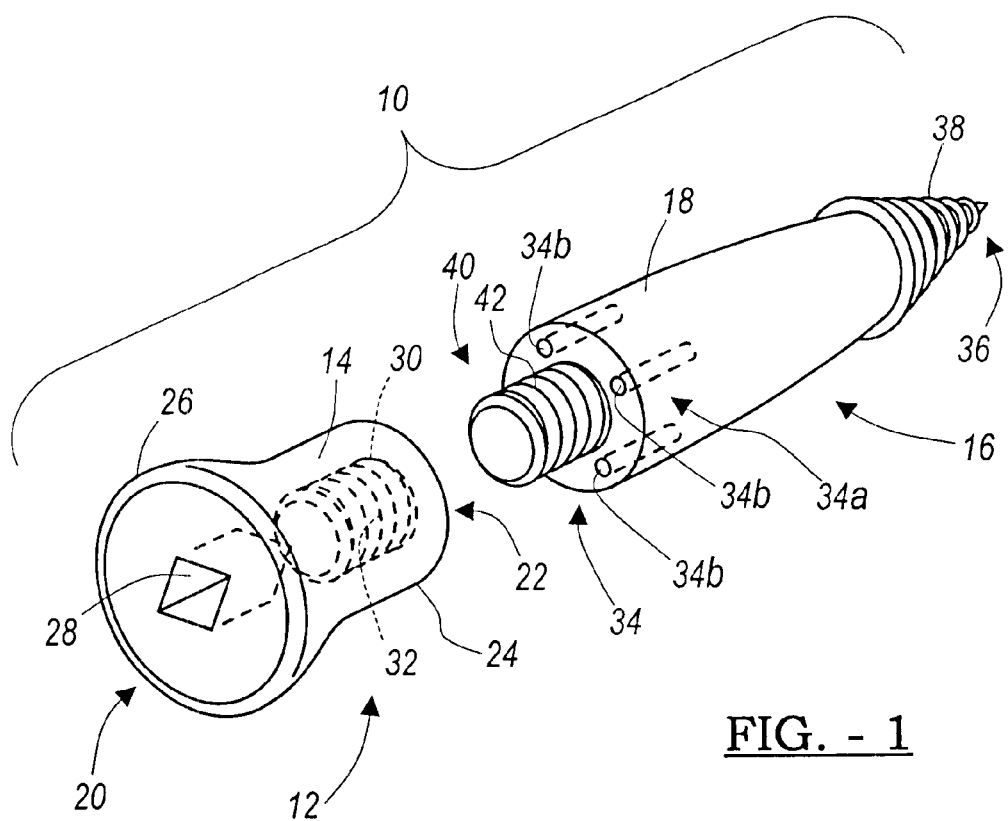
FIG. 1 illustrates an exploded view of an orthopedic fixation system, in accordance with one embodiment of the present invention.
Figure 2:
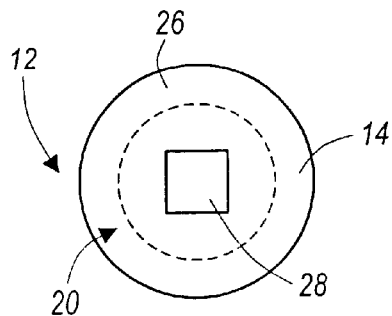
FIG. 2 illustrates a top plan view of the proximal portion of the orthopedic fixation system depicted in FIG. 1, in accordance with one embodiment of the present invention.
Figure 3:
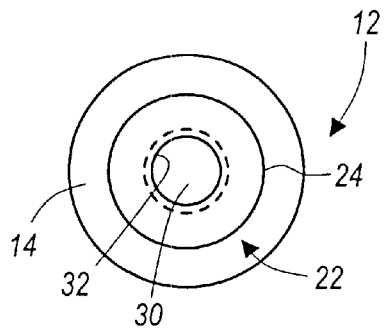
FIG. 3 illustrates a bottom plan view of the proximal portion of the orthopedic fixation system depicted in FIG. 1, in accordance with one embodiment of the present invention.
Figure 4:
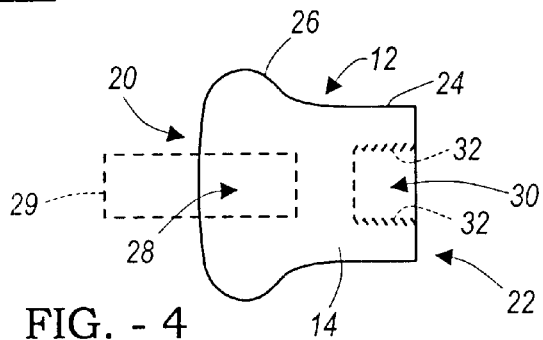
FIG. 4 illustrates an elevational view of the proximal portion of the orthopedic fixation system depicted in FIG. 1, in accordance with one embodiment of the present invention.
Figure 5:
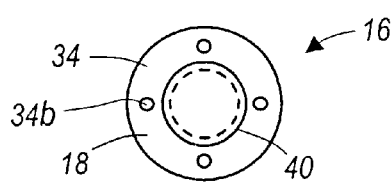
FIG. 5 illustrates a top plan view of the distal portion of the orthopedic fixation system depicted in FIG. 1, in accordance with one embodiment of the present invention.
Figure 6:
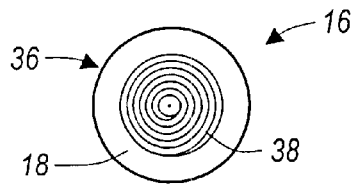
FIG. 6 illustrates a bottom plan view of the distal portion of the orthopedic fixation system depicted in FIG. 1, in accordance with one embodiment of the present invention.

Referring to FIGS. 1–7, there is generally shown an orthopedic fixation system 10, in accordance with one embodiment of the present invention. Although a surgical or bone screw is shown for illustrative purposes, it should be appreciated that any number of different types of surgical devices, such as surgical fasteners, may be practiced with the present invention, including, but not limited to plates, rods, pins, staples.

The system 10 primarily includes a proximal portion 12 comprised of a bioresorbable material 14 and a distal portion 16 comprised of a non-resorbable material 18. Distal portion 16 is substantially elongated as compared to proximal portion 12. Bioresorbable material 14 is preferably comprised of materials selected from the group consisting of hydroxyapatite, polylactic acid, polyglycolic acid, and combinations thereof. Non- resorbable material 18 is preferably comprised of materials selected from the group consisting of stainless steel, titanium, cobalt-chrome alloys, and combinations thereof.

Proximal portion 12 includes a proximal region 20 and a spaced and opposed distal region 22. Proximal region 20 includes a shaft-like portion 24 extending from distal region 22 towards proximal region 20. As shaft portion 24 nears proximal region 20, an adjacent and contiguous head portion 26 is provided. Disposed on the proximal surface of head portion 26 is a recess 28 which is intended to receive a driver member, as will be explained later. Alternatively, instead of employing a recess, an optional raised member, such as a hex-shaped member 29, shown in phantom in FIG. 4, may used to engage a driver member. Disposed on the distal surface of shaft portion 24 is another recess 30, which preferably has a threaded surface 32 thereon, the purpose of which will be explained later.

Distal portion 16 also includes a proximal region 34 and a spaced and opposed distal region 36. An external threaded surface 38 is provided on the distal region 36 of distal portion 16, and is intended to function as a cutting surface for permitting insertion into tissue, such as, but not limited to bone tissue. Proximal region 34 preferably includes a mating member 40 which is intended to selectively mate with recess 30 of proximal portion 12. Preferably, mating member 40 is provided with a threaded surface 42 thereon which corresponds to threaded surface 32 of recess 30. Accordingly, the respective configurations of recess 32 and mating member 40 should be complementary towards one another. Although mating member 40 and recess 32 are shown as being circular and threaded, other configurations are envisioned, as well. Furthermore, a snap-fit appendage (not shown) may be provided on mating member 40 that snaps into a further recess (not shown) on the surface wall of recess 32.

Figure 7:
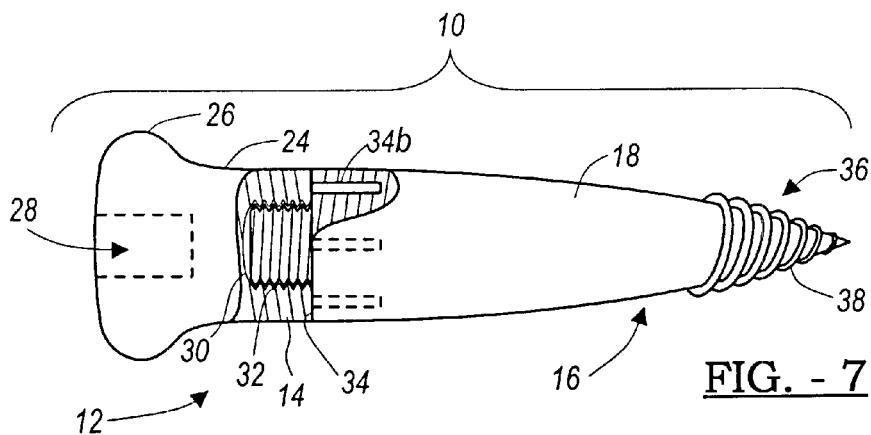
FIG. 7 illustrates an elevational view of the proximal and distal portions of the orthopedic fixation system depicted in FIG. 1 in abutting engagement, in accordance with one embodiment of the present invention.

System 10 is unique in that proximal portion 12 and distal portion 16 need not be joined together (as shown in FIG. 7) in order to initiate the insertion of system 10 into tissue, such as bone tissue, in order to join two bone fragments together, to attach an orthopedic appliance (e.g., bone plate) to and/or into a bone surface, or to accomplish any other suitable orthopedic procedure. That is, distal portion 16 may first be inserted, either partially or substantially completely, and then proximal portion 12 may then be joined to distal portion 16, whereupon system 10 is then fully and completely inserted. In this manner, the torque forces encountered during initial insertion of system 10 into hard bone tissue are not acting upon resorbable proximal portion 12, thus lessening the chances of catastrophic failure of system 10 at resorbable proximal portion 12/non-resorbable distal portion 16 interface.

A non-limiting example of a method of using orthopedic fixation system 10 in conjunction will be described with reference to FIGS. 8–12. In order to facilitate the insertion of the distal portion 16, a rotation facilitation and release facilitation system 34a is preferably provided on the proximal surface of proximal region 34. By way of a non-limiting example, rotation facilitation and release facilitation system 34a preferably includes at least one, preferably at least two, and still more preferably, at least three areas defining recesses 34b located in the proximal surface of the proximal region 34. By way of a non-limiting example, these recesses 34b can mate with a three-pronged driver member 104 having three matching prongs 104a which can then rotate and insert distal portion 16 and then can be easily removed from recesses 34b by simply pulling outwardly away therefrom. In this manner, there is no need to engage threaded mating member 40. This is significant, in that if driver member 104 is used to mate with threaded mating member 40 (e.g., via an internal threaded surface), there would not be a simple way of disengaging driver member 104 from threaded mating member 40 once distal member 16 had been inserted into the bone tissue. To overcome this problem, mating member 40 may be configured as a hex-shaped member, or other suitable configuration, that is capable of disengaging from a corresponding driver member without causing distal member 16 to rotate once inserted into the bone tissue.

In FIG. 8, there is shown a fractured femur head 100 having a pilot hole 102 pre-drilled for receiving the orthopedic fixation system 10. In this view, only distal portion 16 is shown as it will be driven first into pilot hole 102. A suitable driver 104 is shown which preferably mates with recesses 34b, or alternatively, mating member 40.

In FIG. 9, driver member 104 is rotated in direction R (e.g., clockwise) so as to cause distal portion 16 to be driven into pilot hole 102. The torque generated by the rotation acts exclusively on distal portion 16 as it cuts through the bone tissue adjacent to pilot hole 102. Additionally, driver member 104 can be fitted which a device to create a countersink in the surface of the bone tissue.

Figure 10:
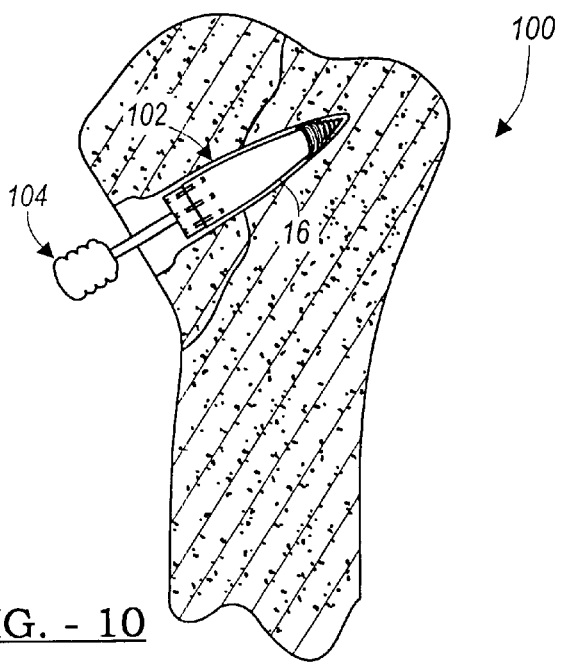
FIG. 10 illustrates a partial sectional view of a distal portion of an orthopedic fixation system fully inserted into a fracture site of a femur head, in accordance with one embodiment of the present invention.

In FIG. 10, distal portion 16 has been substantially fully inserted into pilot hole 102. Note that distal portion 16 extends across both portions of the fracture site, providing outstanding physical support for the fracture site in which proper healing can take place.

Figure 11:
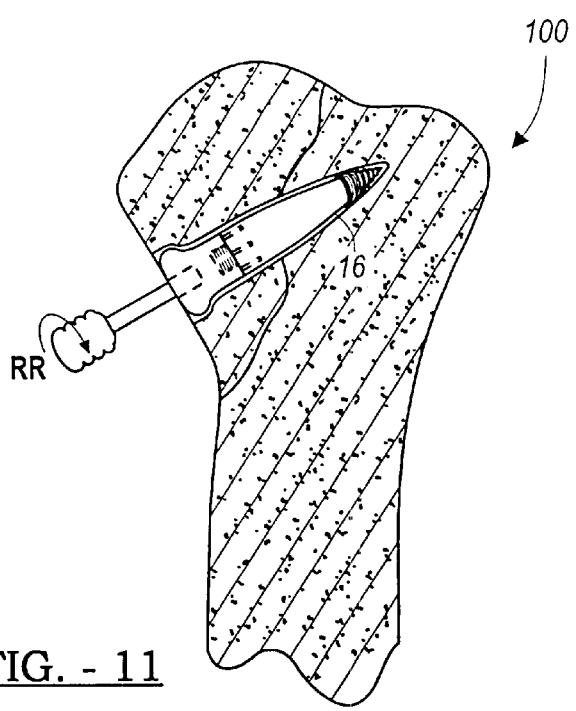
FIG. 11 illustrates a partial sectional view of a proximal portion of an orthopedic fixation system being inserted onto the distal portion of the orthopedic fixation system, in accordance with one embodiment of the present invention.

In FIG. 11, proximal portion 12 is mated to distal portion 16 and another driver member 106 is used to rotate proximal portion 12 in direction RR so as to cause both proximal portion 12 and distal portion 16 to be inserted slightly more into pilot hole 102 until system 10 can no longer be inserted any further into the bone tissue.

Figure 12:
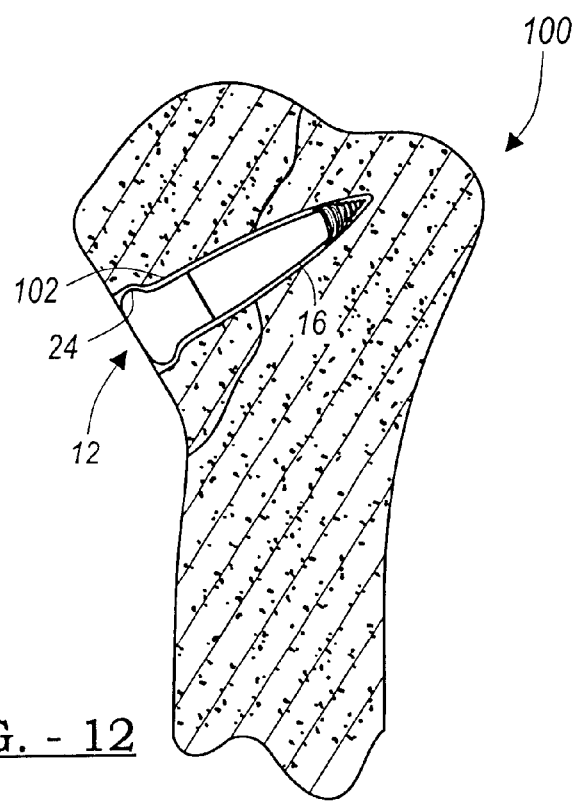
FIG. 12 illustrates a partial sectional view of a fully inserted orthopedic fixation system, in accordance with one embodiment of the present invention.

In FIG. 12, system 10 is shown in its fully inserted position, with head portion 26 of proximal portion 12 being substantially co-planar with the surface of the bone tissue, thus eliminating any tissue irritation concerns previously discussed. Proximal portion 12 will eventually be resorbed by the body over time. New bone tissue will eventually grow into the portion of pilot hole 102 occupied by proximal portion 102, as it gradually resorbs. It should be noted that head portion 26 need not be completely countersunk into the bone tissue, as shown. Occasionally, head portion 26 may protrude slightly above the surface of the bone tissue. Generally, this is not an undesirable condition, as head portion 26 will eventually be resorbed. However, the surgeon may optionally either remove the protruding portion (e.g., with a heat loop or a cutting tool such as a burr) or alternatively, melt the protruding portion so that it assumes a lower profile against the surface of the bone tissue.

It should also be appreciated that the present invention can also be used to affix or fasten orthopedic appliances, such as bone plates and the like, to and/or into bone surfaces. In that case, the orthopedic fixation system of the present invention would be simply driven through the orthopedic appliance (or a provided hole therein), by rotating the various driver members of the present invention, and into the respective bone surface. The orthopedic fixation system of the present invention can be used with resorbable, as well as non-resorbable, orthopedic appliances.

Figure 13:
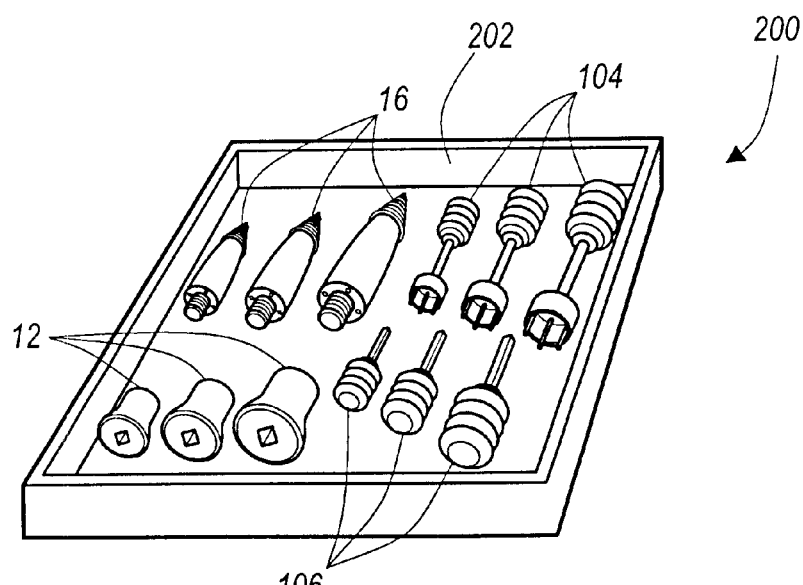
FIG. 13 illustrates a perspective view of a kit containing various sizes of the components of the orthopedic fixation system as well as the driver member, in accordance with one embodiment of the present invention.
Figure 14:
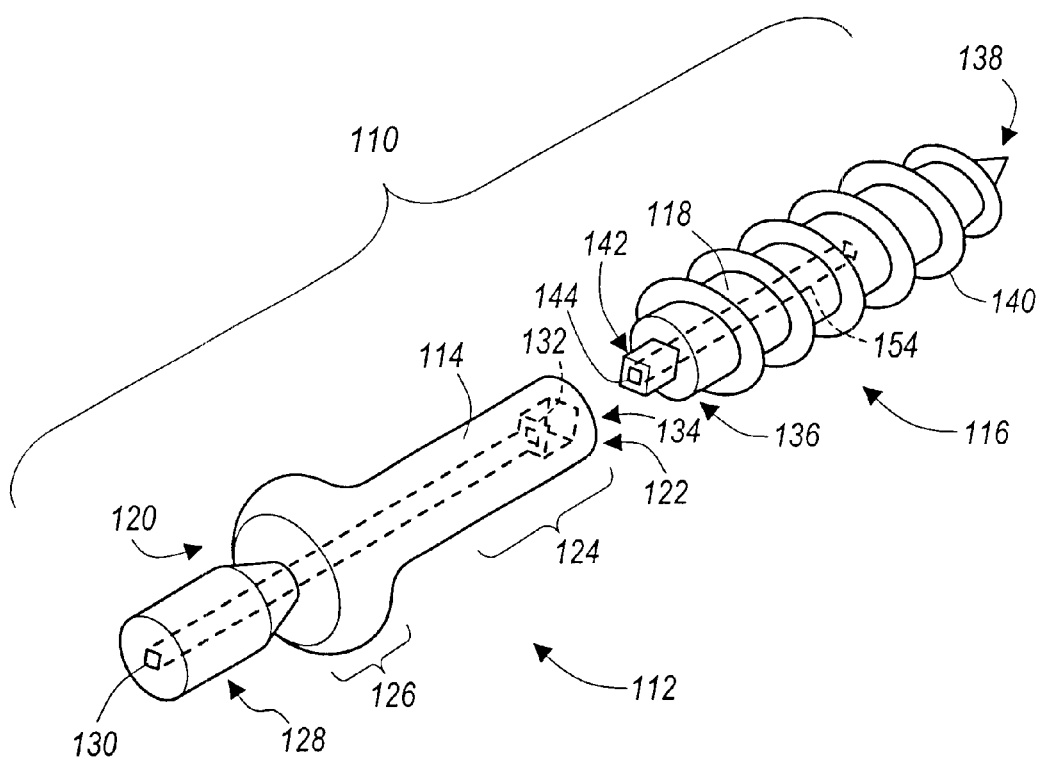
FIG. 14 illustrates an exploded view of an orthopedic fixation system, in accordance with an alternative embodiment of the present invention.

In order to provide the greatest versatility and flexibility to the orthopedic surgeon, the present invention provides various sizes of the aforementioned components of the orthopedic fixation system 10, as well as various driver members 104 and 106, in a surgical kit form, as shown in FIG. 13. Kit 200 includes a receptacle 202 which can neatly, and preferably sterilely, store any number of different size component/driver so that the orthopedic surgeon can have his/her choice as to which size component/driver is appropriate to use. For example, the repair of a fracture of a relatively small bone (e.g., a metatarsal) may require a relatively small orthopedic fixation system 10, whereas the repair of a large bone (e.g., a femur or tibia) may require a relatively large orthopedic fixation system 10. Alternatively, a fracture site might be difficult to reach with one size driver member 104 or 106, but is easily reached with a relatively larger driver member 104 or 106. Kit 200 provides the surgeon with any number of choices as how to approach the orthopedic procedure presented to him/her.

Referring to FIGS. 14–19, there is generally shown an alternative orthopedic fixation system 110, in accordance with an alternative embodiment of the present invention. Although a surgical or bone screw is shown for illustrative purposes, it should be appreciated that any number of different types of surgical devices, such as surgical fasteners, may be practiced with the present invention, including, but not limited to plates, rods, pins, staples.

System 110 primarily includes a proximal portion 112 comprised of a bioresorbable material 114 and a distal portion 116 comprised of a non-resorbable material 118. Bioresorbable material 114 is preferably comprised of materials selected from the group consisting of hydroxyapatite, polylactic acid, polyglycolic acid, and combinations thereof. Non-resorbable material 118 is preferably comprised of materials selected from the group consisting of stainless steel, titanium, cobalt-chrome alloys, and combinations thereof.

Proximal portion 112 includes a proximal region 120 and a spaced and opposed distal region 122. Proximal region 120 includes a shaft-like portion 124 extending from distal region 122 towards proximal region 120. As shaft portion 124 nears proximal region 120, an adjacent and contiguous head portion 126 is provided. Extending above head portion 126 is an optional insertion facilitation member 128, the purpose of which will be explained later.

Extending along the longitudinal axis of proximal portion 112 is a throughbore 130. At the distal surface 132 of proximal member 112 is a recess 134, the purpose of which will be explained later.

Distal portion 116 also includes a proximal region 136 and a spaced and opposed distal region 138. An external threaded surface 140 is provided on substantially the entire external surface of distal portion 116, and is intended to function as a cutting surface for permitting insertion into tissue, such as, but not limited to bone tissue. Proximal region 136 includes a mating member 142 which is intended to selectively mate with recess 134 of proximal portion 112. Accordingly, the respective configurations of recess 134 and mating member 142 should be complementary towards one another. Although mating member 142 and recess 134 are shown as being rectangular, other configurations are envisioned, as well. Furthermore, a snap-fit appendage (not shown) may be provided on mating member 142 that snaps into a further recess (not shown) on the surface wall of recess 134.

Extending along the longitudinal axis of distal portion 116 is a bore 144, which originated on the top surface of mating member 142 and extends approximately halfway along the length of distal portion 116. When proximal portion 112 and distal portion 116 are placed in abutting engagement, throughbore 130 preferably aligns with bore 144, as specifically shown in FIG. 19.

Once proximal portion 112 and distal portion 116 are joined together (as shown in FIG. 19) it is then possible to insert system 110 into tissue, such as bone tissue, in order to join two bone fragments together, to attach an orthopedic appliance (e.g., bone plate) to and/or into a bone surface, or to accomplish any other suitable orthopedic procedure.

However, as opposed to previous hybrid fixation systems where substantial amounts of stress are imparted onto the bioresorbable portion of the fixation system, the present invention endeavors to substantially reduce the amount of stress, especially torque stresses and forces, imparted onto the bioresorbable portion of the fixation system. In this manner, the present invention greatly reduces the incidences of catastrophic failure of the bioresorbable portion of the fixation system.

In order to accomplish this goal, the present invention provides a specialized driver member that imparts the greatest stresses and torque forces on the portion of the fixation system that is best suited to absorb these forces and stresses, i.e., the non-resorbable distal portion.

Figure 20:
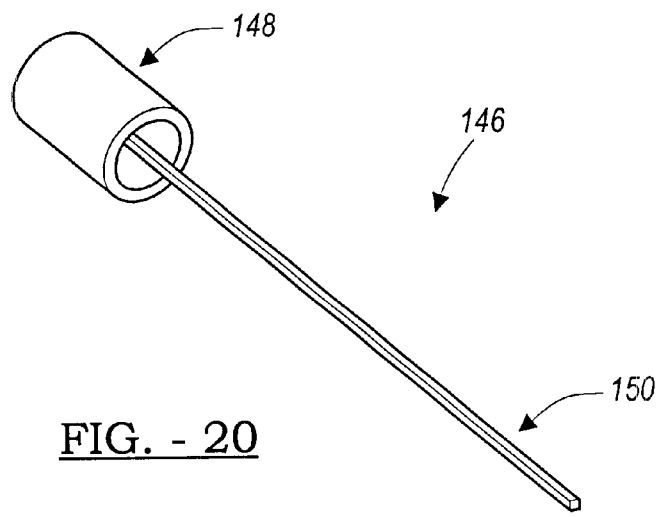
FIG. 20 illustrates a perspective view of an insertion member, in accordance with an alternative embodiment of the present invention.
Figure 21:
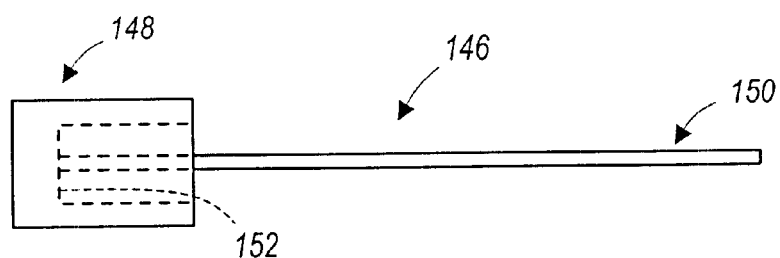
FIG. 21 illustrates an elevational view of the insertion member depicted in FIG. 20, in accordance with an alternative embodiment of the present invention.
Figure 22:
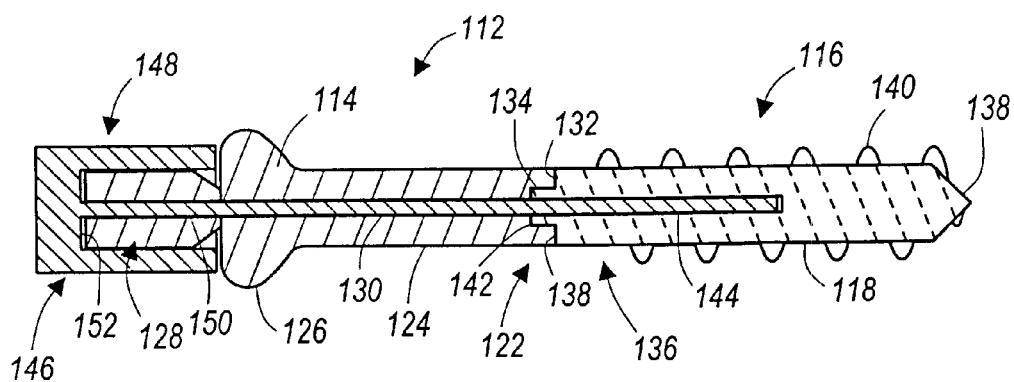
FIG. 22 illustrates an elevational view of the proximal and distal portions of the orthopedic fixation system depicted in FIG. 1, and the driver member depicted in FIGS. 20–21, in abutting engagement, in accordance with an alternative embodiment of the present invention.

Referring to FIGS. 20–22, a driver member 146 includes a cap portion 148 and an elongated appendage portion 150 extending from an internal surface 152 of cap portion 148.

The purpose of elongated appendage portion 150 is to engage an internal surface of bore 144 of distal portion 116. Optionally, elongated appendage portion 150 can also engage an internal surface of throughbore 130 of proximal portion 112. In order for elongated appendage portion 150 to be able to engage an internal surface of bore 144 of distal portion 116, it must first be inserted into throughbore 130 of proximal portion 112 and then preferably fully inserted into bore 144 of distal portion 116.

In order to generate the proper amount of torque necessary to insert fixation system 110 into bone tissue, bore 144 is preferably provided with an anti-rotation device 154, such as, but not limited to a rectangular or hex-shaped internal surface, as opposed to a circular internal surface. Preferably, elongated appendage portion 150 is provided with a complementary external surface that corresponds to the internal surface of bore 144. For example, if bore 144 is hex-shaped, elongated appendage portion 150 should be hex-shaped, if bore 144 is rectangularly-shaped, elongated appendage portion 150 should be rectangularly-shaped, and so forth.

As previously mentioned, throughbore 130 may also be adapted to engage elongated appendage portion 150, as well. For example, if bore 144 and elongated appendage portion 150 are hex-shaped then throughbore 130 should be hex-shaped, if bore 144 and elongated appendage portion 150 are rectangularly-shaped then throughbore 130 should be rectangularly-shaped, and so forth. However, in order to avoid any substantial stresses and forces acting upon throughbore 130, it may optionally be provided with a slightly larger diameter than the diameter of elongated appendage portion 150 so as to avoid any contact therewith. In this manner, as driver member 146 is rotated, the torque generated will substantially be acting on distal portion 116, as opposed to proximal portion 112. Therefore, the probability that a catastrophic failure of proximal portion 112 will occur at the interface between proximal portion 112 and distal portion 116 is greatly reduced.

Internal surface 152 of cap portion 148 is substantially hollow, with the exception of elongated appendage portion 150 emanating therefrom. Because it is hollow, it is able to snuggly fit over optional insertion facilitation member 128, although not so snuggly that driver member 146 can not be easily removed. In this manner, as driver member 146 is rotated, the torque generated will substantially be acting on optional insertion facilitation member 128 and to a much greater degree upon distal portion 116, as opposed to proximal portion 112. Even if throughbore 130 is optionally provided with a slightly larger diameter than the diameter of elongated appendage portion 150 as previously described, driver member 146 will not wobble, because it is held snuggly by bore 144 of distal portion 116 and internal surface 152 of cap 148 is held snuggly against optional insertion facilitation member 128. Therefore, the probability that a catastrophic failure of proximal portion 112 will occur at the interface between proximal portion 112 and distal portion 116 is greatly reduced.

A non-limiting example of a method of using the orthopedic fixation system 110 in conjunction with driver member 146 will be described with reference to FIGS. 23–27.

Figure 23:
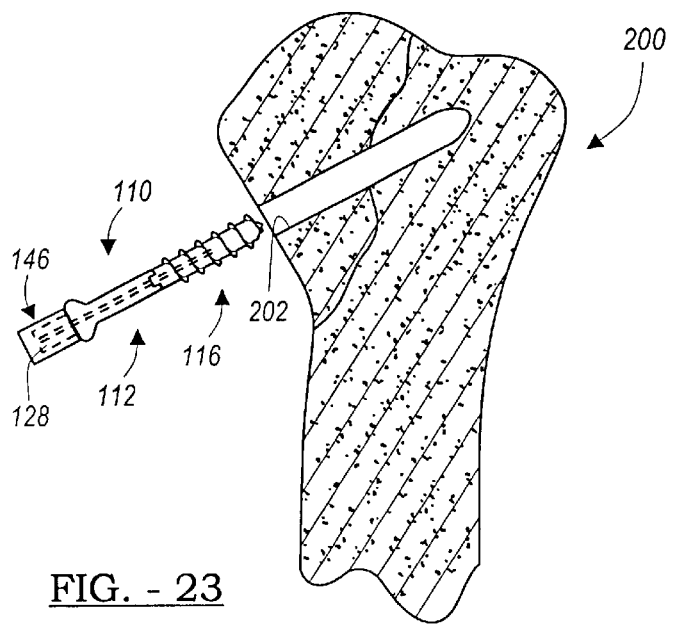
FIG. 23 illustrates a partial sectional view of an orthopedic fixation system about to be inserted into a fracture site of a femur head, in accordance with an alternative embodiment of the present invention.

In FIG. 23, there is shown a fractured femur head 200 having a pilot hole 202 pre-drilled for receiving the orthopedic fixation system 110. In this view, proximal portion 112 and distal portion 116 are joined together with driver member 146 associated therewith.

Figure 24:
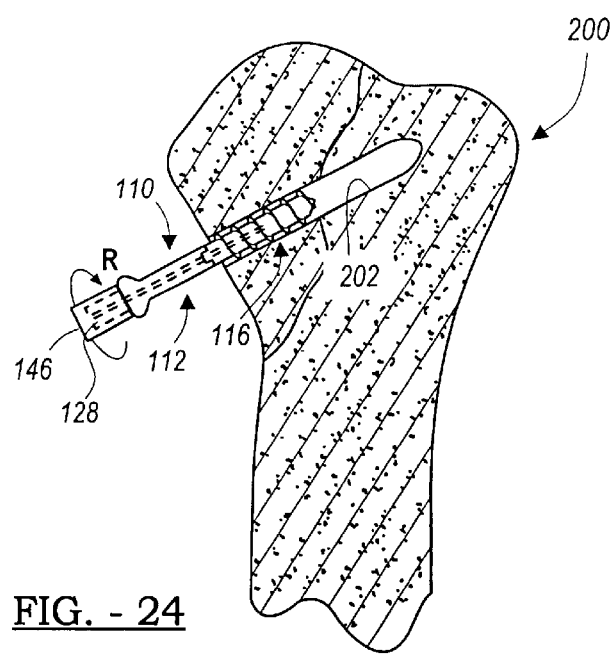
FIG. 24 illustrates a partial sectional view of an orthopedic fixation system partially inserted into a fracture site of a femur head, in accordance with an alternative embodiment of the present invention.

In FIG. 24, driver member 146 is rotated in direction R (e.g., clockwise) so as to cause orthopedic fixation system 110 to be driven into pilot hole 202. The torque generated by the rotation acts primarily on distal portion 116 as it cuts through the bone tissue adjacent to pilot hole 202.

Figure 25:
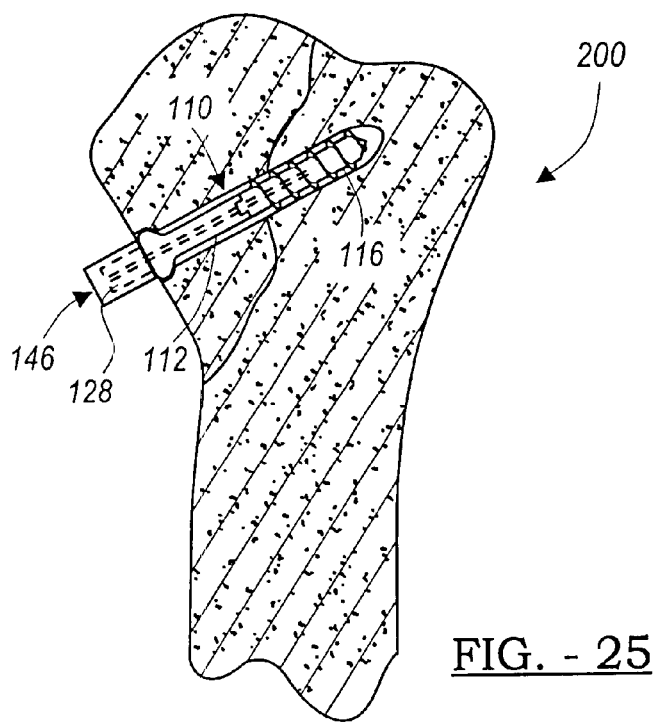
FIG. 25 illustrates a partial sectional view of an orthopedic fixation system fully inserted into a fracture site of a femur head, in accordance with an alternative embodiment of the present invention.

In FIG. 25, driver member 146 can no longer be rotated anymore, indicating that orthopedic fixation system 110 has been fully inserted into pilot hole 202.

Figure 26:
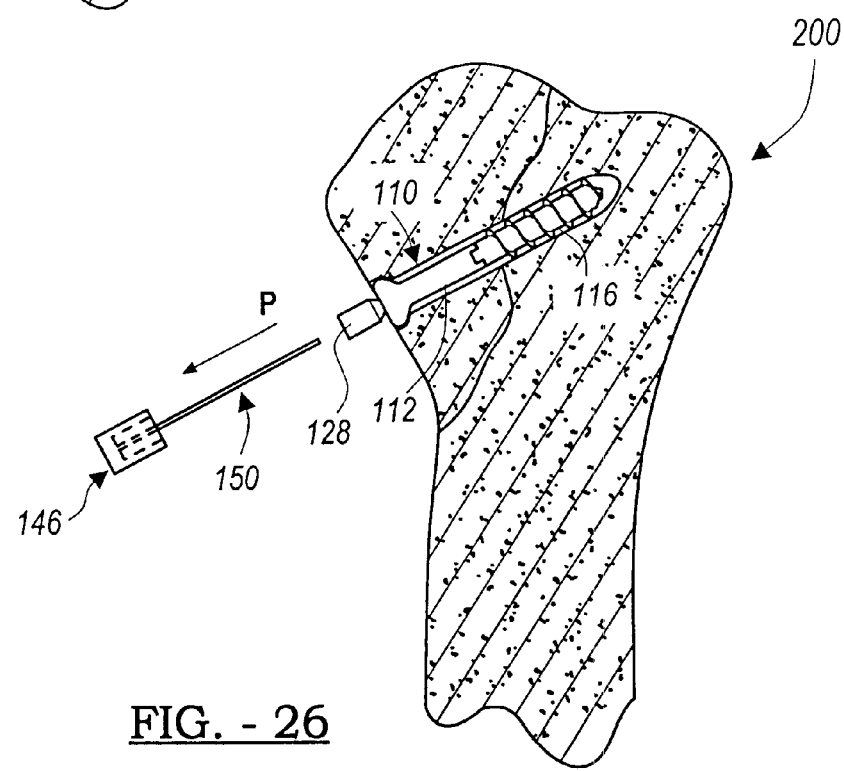
FIG. 26 illustrates a partial sectional view of a driver member being removed from a fully inserted orthopedic fixation system, in accordance with an alternative embodiment of the present invention.

In FIG. 26, driver member 146 is removed from orthopedic fixation system 110 by applying a gentle pulling force in direction P, exposing elongated appendage portion 150.

Figure 27:
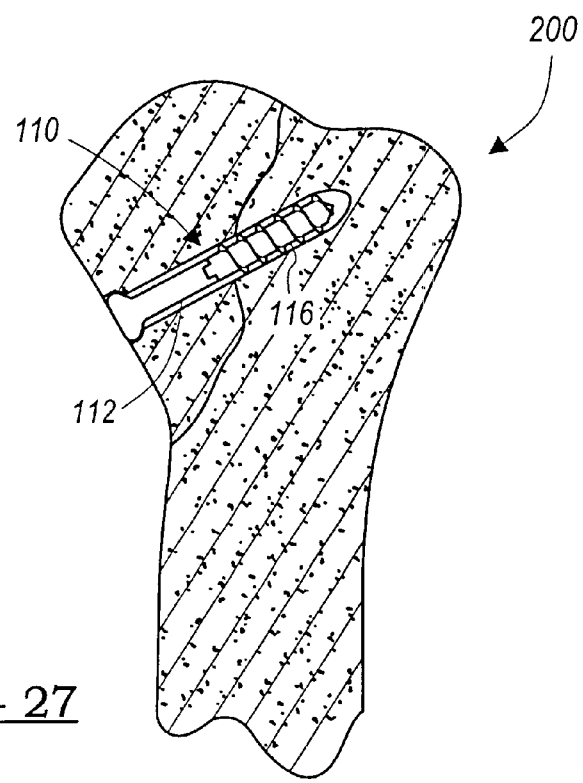
FIG. 27 illustrates a partial sectional view of a fully inserted orthopedic fixation system wherein the optional insertion facilitation member has been removed, in accordance with an alternative embodiment of the present invention.

In FIG. 27, optional insertion facilitation member 128 may optionally be removed (e.g., with a heat loop), if the clinical setting requires so. Otherwise, optional insertion facilitation member 128, as well as proximal portion 112, will eventually be resorbed by the body over time. New bone tissue will eventually grow into the portion of pilot hole 202 occupied by proximal portion 112, as it gradually resorbs.

It should also be appreciated that the present invention can also be used to affix or fasten orthopedic appliances, such as bioresorbable bone plates and the like, to and/or into bone surfaces. In that case, the orthopedic fixation system of the present invention would be simply driven through the resorbable orthopedic appliance (or a provided hole therein), by rotating the driver member of the present invention, and into the respective bone surface. After insertion is complete, the driver member of the present invention would be removed from the orthopedic fixation system of the present invention. As the resorbable orthopedic appliance resorbs, the resorbable portion of the orthopedic fixation system of the present invention would also resorb, although perhaps at a slower rate to prevent premature detachment of the resorbable orthopedic appliance from the bone surface.

Figure 28:
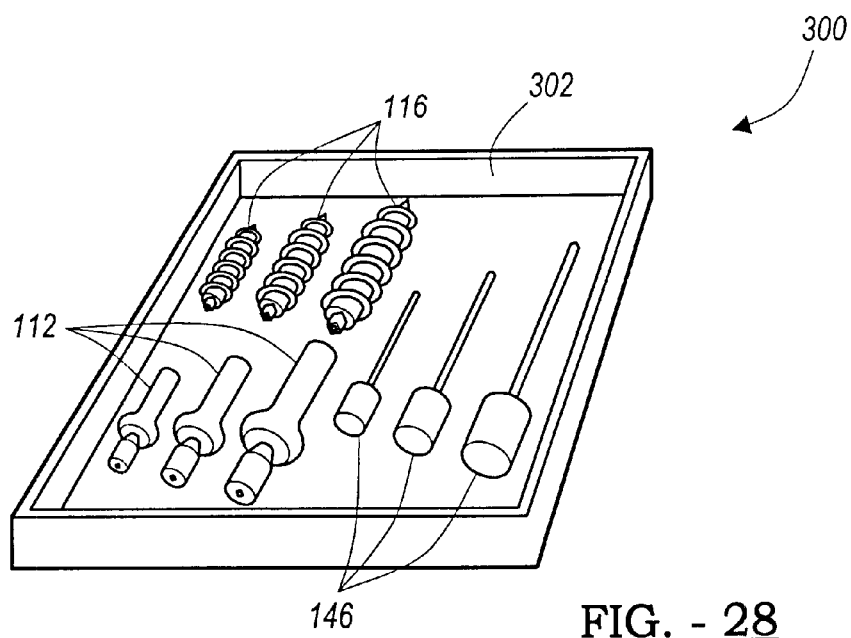
FIG. 28 illustrates a perspective view of a kit containing various sizes of the components of the orthopedic fixation system as well as the driver member, in accordance with an alternative embodiment of the present invention.

In order to provide the greatest versatility and flexibility to the orthopedic surgeon, the present invention provides various sizes of the aforementioned components of orthopedic fixation system 110, as well as driver member 146, in a surgical kit form, as shown in FIG. 28. Kit 300 includes a receptacle 302 which can neatly, and preferably sterilely, store any number of different size component/driver so that the orthopedic surgeon can have his/her choice as to which size component/driver is appropriate to use. For example, the repair of a fracture of a relatively small bone (e.g., a metatarsal) may require a relatively small orthopedic fixation system 110, whereas the repair of a large bone (e.g., a femur or tibia) may require a relatively large orthopedic fixation system 110. Alternatively, a fracture site might be difficult to reach with one size driver member 146, but is easily reached with a relatively larger driver member 146. Kit 300 provides the surgeon with any number of choices as how to approach the orthopedic procedure presented to him/her.

The foregoing description is considered illustrative only of the principles of the invention. Furthermore, because numerous modifications and changes will readily occur to those skilled in the art, it is not desired to limit the invention to the exact construction and process shown as described above. Accordingly, all suitable modifications and equivalents that may be resorted to that fall within the scope of the invention as defined by the claims that follow.

What is claimed is:

1. An orthopedic fixation system, comprising:
   a first head member comprised of a bioresorbable material, the first head member having a distal and proximal region, the distal region having a threaded portion and the proximal region having a first diameter; and
   a second shaft member comprised of a non-resorbable material, the second shaft member having a distal and proximal region, the proximal region having a threaded portion that threadably mates with the threaded portion of the first head member upon threadably rotating the first head member relative to the second shaft member in a first direction, the second shaft member having a second diameter;
   wherein the distal region of the first head member is adapted to selectively mate with the proximal region of the second shaft member;
   wherein the second shaft member is substantially elongated with respect to the first head member;
   wherein the distal region of the second shaft member is provided with an external threaded surface thereon;
   wherein the first diameter of the first head member is larger than the second diameter of the second shaft member.

2. The invention according to claim 1, wherein the first member is a head portion of a bone screw.

3. The invention according to claim 1, wherein the bioresorbable material is comprised of materials selected from the group consisting of hydroxyapatite, polylactic acid, polyglycolic acid, and combinations thereof.

4. The invention according to claim 1, wherein the second member is a shaft portion of a bone screw.

5. The invention according to claim 1, wherein the second member is comprised of a metallic material.

6. The invention according to claim 1, further comprising an area defining a receptacle disposed in the distal region of the first member.

7. The invention according to claim 6, further comprising a connection member disposed on the proximal region of the second member.

8. The invention according to claim 7, wherein the connection member threadably mates with the receptacle.

9. The invention according to claim 1, further comprising an area defining a receptacle disposed in the proximal region of the first member.

10. The invention according to claim 9, further comprising a driver member adapted to be received by the receptacle disposed in the proximal region of the first member.

11. The invention according to claim 1, wherein the orthopedic fixation system fixes a first bone fragment to a second bone fragment.

12. The invention according to claim 11, wherein the second member extends across the first bone fragment and the second bone fragment.

13. The invention according to claim 1, wherein the orthopedic fixation system fixes an orthopedic appliance to a bone surface.

14. The invention according to claim 1, wherein the first member is substantially coplanar with the surface of a bone surface.

15. An orthopedic fixation system kit, comprising:
  a receptacle, the receptacle containing:
  a plurality of first members comprised of a bioresorbable material and each having a different size, each of the first members having a distal and proximal region, each distal region having a threaded portion;
  a plurality of second members comprised of a non-resorbable material and each having a different size, each of the second members having a distal and proximal region, each proximal region having a threaded portion that threadably mates with the threaded portion of the first member upon threadably rotating the first member relative to the second member in a first direction;
  wherein the distal region of each first member is adapted to selectively mate with the proximal region of each second member that has a corresponding size;
  wherein the second member is substantially elongated with respect to the first member;
  wherein the distal region of the second member is provided with an external threaded surface thereon;
  wherein the second member is operable to threadably engage bone upon rotating the second member in a second direction, where the first direction is opposite the second direction.

16. The invention according to claim 15, wherein the first members are head portions of a bone screw.

17. The invention according to claim 15, wherein the bioresorbable material is comprised of materials selected from the group consisting of hydroxyapatite, polylactic acid, polyglycolic acid, and combinations thereof.

18. The invention according to claim 15, wherein the second members are shaft portions of a bone screw.

19. The invention according to claim 15, wherein the second members are comprised of a metallic material.

20. The invention according to claim 15, further comprising an area defining a receptacle disposed in the distal regions of the first members.

21. The invention according to claim 20, further comprising a connection member disposed on the proximal regions of the second members.

22. The invention according to claim 21, wherein the connection member threadably mates with the receptacle.

23. The invention according to claim 15, further comprising an area defining a receptacle disposed in the proximal regions of the first members.

24. The invention according to claim 23, further comprising a driver member adapted to be received by the receptacle disposed in the proximal regions of the first members.

25. The invention according to claim 15, wherein the orthopedic fixation system fixes a first bone fragment to a second bone fragment.

26. The invention according to claim 25, wherein the second members extend across the first bone fragment and the second bone fragment.

27. The invention according to claim 15, wherein the orthopedic fixation system fixes an orthopedic appliance to a bone surface.

28. The invention according to claim 15, wherein the first member is substantially coplanar with the surface of a bone surface.

29. A method of affixing an orthopedic device to bone tissue, comprising:
  providing a fixation device, including:
    a first member comprised of a bioresorbable material, the first member having a distal and proximal region, the distal region having a threaded portion and the proximal region having a first diameter; and
    a second member comprised of a non-resorbable material, the second member having a distal and proximal region, the proximal region having a threaded portion, the second member having a second diameter, the first diameter being larger than the second diameter;
  wherein the distal region of the first member is adapted to threadably mate with the proximal region of the second member upon rotating the first member relative to the second member in a first direction;
  wherein the second member is substantially elongated with respect to the first member;
  wherein the distal region of the second member is provided with an external threaded surface thereon;
  providing a driver member adapted to be engaged by either the first member or the second member; and
  applying a rotary force to the driver member so as to cause either the first member or the second member to be inserted into the bone tissue such that either the first member or the second member is brought into abutting engagement with the bone tissue.

30. The invention according to claim 29, wherein the second member is inserted into the bone tissue and then the first member is inserted into the bone tissue.

31. The method according to claim 29, wherein the driver can disengage from the second member without causing the second member to rotate.

32. A method of joining two bone fragments, comprising:
  providing a fixation device, including:
    a first member comprised of a bioresorbable material, the first member having a distal and proximal region, the distal region having a threaded portion and the proximal region having a first diameter; and a second member comprised of a non-resorbable material, the second member having a distal and proximal region, the proximal region having a threaded portion, the second member having a second diameter, the first diameter being larger than the second diameter;

wherein the distal region of the first member is adapted to threadably mate with the proximal region of the second member upon rotating the first member relative to the second member in a first direction;

wherein the second member is substantially elongated with respect to the first member;

wherein the distal region of the second member is provided with an external threaded surface thereon;

providing a driver member adapted to engage either the first member or the second member; and applying a rotary force to the driver member so as to cause either the first member or the second member to be inserted into at least one of the bone fragments so as bring both of the bone fragments together into abutting engagement.

33. The invention according to claim 32, wherein the second member is inserted into the bone tissue and then the first member is inserted into the bone tissue.

34. The method according to claim 32, wherein the driver can disengage from the second member without causing the second member to rotate.

35. An orthopedic fixation system, comprising:

a first member comprised of a bioresorbable material, the first member having a distal and proximal region; and a second member comprised of a non-resorbable material, the second member having a distal and proximal region;

wherein the distal region of the first member is adapted to selectively mate with the proximal region of the second member;

wherein the first member is provided with a throughbore extending along a longitudinal axis thereof;

wherein the second member is provided with a closed-end bore extending from the proximal region towards the distal region thereof, the closed-end bore including an anti-rotation device;

wherein the second member is provided with an external threaded surface thereon.

36. The invention according to claim 35, wherein the first member is a shaft portion of a bone screw.

37. The invention according to claim 35, wherein the first member is an integral head and shaft portion of a bone screw.

38. The invention according to claim 35, wherein the bioresorbable material is comprised of materials selected from the group consisting of hydroxyapatite, polylactic acid, polyglycolic acid, and combinations thereof.

39. The invention according to claim 35, wherein the throughbore and the bore are substantially aligned.

40. The invention according to claim 35, wherein the bore includes an anti-rotation device.

41. The invention according to claim 35, wherein the second member is comprised of a metallic material.

42. The invention according to claim 35, further comprising a driver member adapted to be received simultaneously within the throughbore of the first member and the bore of the second member.

43. The invention according to claim 35, wherein the orthopedic fixation system fixes a first bone fragment to a second bone fragment.

44. The invention according to claim 35, wherein the orthopedic fixation system fixes an orthopedic appliance to a bone surface.

45. An orthopedic fixation system, comprising:

a first head member comprised of a bioresorbable material, the first head member having a distal and proximal region, the distal region having a threaded portion and the proximal region having a first diameter;

a second shaft member comprised of a non-resorbable material, the second shaft member having a distal and proximal region, the proximal region having a threaded portion that threadably mates with the threaded portion of the first head member upon threadably rotating the first head member relative to the second shaft member in a first direction, the second shaft member having a second diameter;

wherein the distal region of the first head member is adapted to selectively mate with the proximal region of the second shaft member;

wherein the first head member is provided with a throughbore extending along a longitudinal axis thereof;

wherein the second shaft member is provided with a bore extending from the proximal region towards the distal region thereof;

wherein the second shaft member is provided with an external threaded surface thereon; and a driver member adapted to be received simultaneously within the throughbore of the first head member and the bore of the second shaft member and wherein the first diameter of the first head member is larger than the second diameter of the second shaft member.

46. The invention according to claim 45, wherein the first member is a shaft portion of a bone screw.

47. The invention according to claim 45, wherein the first member is an integral head and shaft portion of a bone screw.

48. The invention according to claim 45, wherein the bioresorbable material is comprised of materials selected from the group consisting of hydroxyapatite, polylactic acid, polyglycolic acid, and combinations thereof.

49. The invention according to claim 45, wherein the throughbore and the bore are substantially aligned.

50. The invention according to claim 45, wherein the bore includes an anti-rotation device.

51. The invention according to claim 45, wherein the second member is comprised of a metallic material.

52. The invention according to claim 45, wherein the orthopedic fixation system fixes a first bone fragment to a second bone fragment.

53. The invention according to claim 45, wherein the orthopedic fixation system fixes an orthopedic appliance to a bone surface.

54. An orthopedic fixation system kit, comprising:

a receptacle, the receptacle containing:

a plurality of first members comprised of a bioresorbable material and each having a different size, each of the first members having a distal and proximal region;

a plurality of second members comprised of a non-resorbable material and each having a different size, each of the second members having a distal and proximal region;

wherein the distal region of each first member is adapted to selectively mate with the proximal region of each second member that has a corresponding size;

wherein each first member is provided with a throughbore extending along a longitudinal axis thereof;

wherein each second member is provided with a closed-end bore extending from the proximal region towards the distal region thereof;

wherein each second member is provided with an external threaded surface thereon; and at least one driver member adapted to be received simultaneously within the throughbore of each first member and the closed-end bore of each second member, wherein the driver member applies rotation torque to only substantially the second member.

55. The invention according to claim 54, wherein the first members are shaft portions of a bone screw.

56. The invention according to claim 54, wherein the first members are integral head and shaft portions of a bone screw.

57. The invention according to claim 54, wherein the bioresorbable material is comprised of materials selected from the group consisting of hydroxyapatite, polylactic acid, polyglycolic acid, and combinations thereof.

58. The invention according to claim 54, wherein the throughbore and the bore are substantially aligned.

59. The invention according to claim 54, wherein the bore includes an anti-rotation device.

60. The invention according to claim 54, wherein the second members are comprised of a metallic material.

61. The invention according to claim 54, wherein the orthopedic fixation system fixes a first bone fragment to a second bone fragment.

62. The invention according to claim 54, wherein the orthopedic fixation system fixes an orthopedic appliance to a bone surface.

63. A method of affixing an orthopedic device to bone tissue, comprising:

providing a fixation device, including:

a first member comprised of a bioresorbable material, the first member having a distal and proximal region; and a second member comprised of a non-resorbable material, the second member having a distal and proximal region;

wherein the distal region of the first member is adapted to selectively mate with the proximal region of the second member;

wherein the first member is provided with a throughbore extending along a longitudinal axis thereof;

wherein the second member is provided with a closed-end bore extending from the proximal region towards the distal region thereof;

wherein the second member is provided with an external threaded surface thereon;

providing a driver member adapted to be received simultaneously within the throughbore of the first member and the closed-end bore of the second member; and applying a rotary force to the driver member so as to cause the fixation device to be inserted into the bone tissue such that the orthopedic device is brought into abutting engagement with the bone tissue and substantially all of the tortional force is applied to the second member as the fixation device is inserted into the bone.

64. A method of joining two bone fragments, comprising:

providing a fixation device, including:

a first member comprised of a bioresorbable material, the first member having a distal and proximal region; and a second member comprised of a non-resorbable material, the second member having a distal and proximal region;

wherein the distal region of the first member is adapted to selectively mate with the proximal region of the second member;

wherein the first member is provided with a throughbore extending along a longitudinal axis thereof;

wherein the second member is provided with a closed-end bore extending from the proximal region towards the distal region thereof;

wherein the second member is provided with an external threaded surface thereon;

providing a driver member adapted to be received simultaneously within the throughbore of the first member and the closed-end bore of the second member; and applying a rotary force to the driver member so as to cause the fixation device to be inserted into both of bone fragments so as bring both of the bone fragments together into abutting engagement and substantially all of the tortional force is applied to the second member as the fixation device is inserted into the bone.

* * * * *

UNITED STATES PATENT AND TRADEMARK OFFICE
CERTIFICATE OF CORRECTION

PATENT NO.    : 6,471,707 B1                                                              Page 1 of 1
DATED         : October 29, 2003
INVENTOR(S)   : Miller et al.

It is certified that error appears in the above-identified patent and that said Letters Patent is hereby corrected as shown below:

Column 1,
Line 59, "it's" should be -- its --.

Column 2,
Line 7, "disclose" should be -- discloses --.
Line 28, "disclose" should be -- discloses --.
Line 40, delete "the".

Column 5,
Line 15, after "of" insert -- the --.

Column 8,
Line 50, "which" should be -- with --.

Column 14,
Lines 58-60, claim 30, claim cancelled -- see Notice of Allowance dated 8/12/02 --.

Column 15,
Line 21, after "as" insert -- to --.

Column 18,
Line 40, after "as" insert -- to --.

Signed and Sealed this

Fifth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,471,707 B1
DATED : October 29, 2002
INVENTOR(S) : Miller et al.

It is certified that error appears in the above-identified patent and that said Letters Patent is hereby corrected as shown below:

Column 1,
Line 59, "it's" should be -- its --.

Column 2,
Line 7, "disclose" should be -- discloses --.
Line 28, "disclose" should be -- discloses --.
Line 40, delete "the".

Column 5,
Line 15, after "of" insert -- the --.

Column 8,
Line 50, "which" should be -- with --.

Column 14,
Lines 58-60, claim 30, claim cancelled -- see Notice of Allowance dated 8/12/02 --.

Column 15,
Line 21, after "as" insert -- to --.

Column 18,
Line 40, after "as" insert -- to --.

This certificate supersedes Certificate of Correction issued August 5, 2003.

Signed and Sealed this

Eighteenth Day of November, 2003

JAMES E. ROGAN
*Director of the United States Patent and Trademark Office*